United States Patent
Van Valkenburg

(10) Patent No.: US 6,346,713 B1
(45) Date of Patent: Feb. 12, 2002

(54) METHOD AND INSTALLATION FOR INSPECTING AN ARTICLE FOR DEFECTS

(75) Inventor: Antonius Ludovicus Gerardus Van Valkenburg, Berkel en Rodenrijs (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/446,305
(22) PCT Filed: Jun. 22, 1998
(86) PCT No.: PCT/NL98/00356
  § 371 Date: Dec. 20, 1999
  § 102(e) Date: Dec. 20, 1999
(87) PCT Pub. No.: WO98/59236
  PCT Pub. Date: Dec. 30, 1998

(30) Foreign Application Priority Data
Jun. 23, 1997 (NL) ............................................... 1006378

(51) Int. Cl.[7] ............................................... G01N 21/86
(52) U.S. Cl. ............... 250/559.45; 250/228; 356/239.1; 356/237.1; 356/236
(58) Field of Search ........................... 250/228, 559.45, 250/559.46, 559.48, 559.49; 356/236, 237.1, 237.2, 239.1, 239.7, 429, 430, 431, 364, 369, 445

(56) References Cited

U.S. PATENT DOCUMENTS 4,378,159 A * 3/1983 Galbraith .................. 356/237.6
4,626,101 A * 12/1986 Ogawa et al. .......... 250/559.49

FOREIGN PATENT DOCUMENTS

| DE | 39 26 349 | 2/1991 |
| EP | 0 146 005 | 6/1985 |
| EP | 0 327 425 | 8/1989 |

* cited by examiner

Primary Examiner—Stephone B. Allen
(74) Attorney, Agent, or Firm—Young & Thompson

(57) ABSTRACT

Method for inspecting an article for defects, light scattered by the article is collected. A defect in the article gives rise to a pulse scanning response signal, which is fed to a processing unit. The light beam has a wavelength such that the article is transparent thereto. At least two scanning response signals are obtained, which are associated with focal points at different focal depths in the article. The location of the defect in the direction of the light beam is determined from the steepness of the front and rear flanks of the pulse scanning response signals. By this means it is possible to determine whether a defect is on or in the article. The at least two scanning response signals can be obtained by scanning the article at least twice, with different focal depth for each scan.

17 Claims, 3 Drawing Sheets

METHOD AND INSTALLATION FOR INSPECTING AN ARTICLE FOR DEFECTS

The invention relates to a method for inspecting an article for defects, wherein the article is scanned by means of a scanning light beam, the light scattered by the article is collected and the collected light is converted into an electrical scanning response signal which is fed to a processing unit for processing the scanning response signals, a defect in the article giving rise to a pulse in the scanning response signal.

An installation of this type is disclosed in European Patent Application EP-A 0 146 005.

In the case of the installation described in the above-mentioned European Patent application, a light source in the form of a laser is used which directs a scanning light beam onto that face on one side of an article to be inspected facing said beam and focuses said beam on the surface thereof. A collection device in the form of an integrating sphere is also used. The scanning light beam enters the integrating sphere through an opening and leaves the sphere through an opposite opening in the sphere and is incident, as a focused beam, on the front face of the article. The light beam is directed at an angle onto the face of the article and the reflected light leaves the sphere via an opening which is located alongside the light beam inlet opening in the integrating sphere. The light which is scattered by the article, and in particular by a defect, is collected by the integrating sphere on a photoelectric converter, from the output of which an electrical scanning response signal can be obtained. If there is a defect, this causes a pulse scanning response signal to be generated. The scanning response signals are fed to a processing unit to determine whether or not there is a defect on the surface of the article.

All that is determined with this known installation is whether or not there is a defect on the surface of the article.

The aim of the invention is to provide a method of the type indicated in the preamble by means of which the location in the direction of the light beam, as well as in a plane perpendicular to the direction of the light beam of the defect in the article can also be determined.

Said aim is achieved according to the invention in that the light beam has a wavelength such that the article is transparent thereto, in that at least two scanning response signals are obtained, each of which being associated with a focal point located in the direction of the light beam at a different depth in the article, and in that the location of the defect in the direction of the light beam is determined from the steepness of the front and rear flanks of the pulses in the scanning response signals. By this means it is possible, for example, to determine whether a defect is on or in the article, so that a decision can be taken as to whether there is any point in cleaning.

In DE-A-39 26 349 a method and apparatus for inspecting articles for defects is described, in which it is known per sé to use 2 response pulses when the article is scanned. However, the depth of a defect in the article is determined from the distance between said response pulses or the amplitude of a response signal.

In a further development of the invention, the at least two scanning response signals are obtained by scanning the article at least twice, the scanning light beam having a different focal depth for each scan.

The use of scanning light beams of different wavelengths and with different focal depths also offers advantages for obtaining a number of scanning response signals. In this case one group of scanning light beams can be directed onto one side of the article and the other group of scanning light beams onto the other side of the article, in order to save space.

The location of a defect can be determined by interpolation of the focal depths between two test results for the steepness of the pulse scanning response signals.

In another embodiment the focal depth of the scanning light beam is gradually increased in the direction of said beam during repeated scanning of the article, the focal depth which is associated with the pulse scanning response signal having the steepest flanks being determined and used as an indication of the depth of the defect.

The invention also relates to an installation for inspecting an article for defects, comprising an article holder for holding an article to be inspected in an inspection plane, a light source, which emits a scanning light beam for scanning the article to be inspected, a collection device for collecting the light scattered by the article, a converter for converting the collected light into an electrical scanning response signal and a defect in the article giving rise to a pulse in the scanning response signal, and a processing unit connected to the output of the converter for processing the scanning response signal. This installation is characterised in that the scanning light beam has a wavelength such that the article is transparent to said beam, that means are present for obtaining at least two scanning response signals, each of which being associated with a focal point located in the direction of the scanning light beam at different depth in the article, and in that the processing unit is provided with a flank steepness measuring device for measuring the steepness of the front or rear flanks of the pulses in the scanning response signals fed thereto, and an evaluation device for determining the location of a defect from the measured flank steepnesses.

Illustrative embodiments of the invention which are preferably to be implemented are described in the further appended dependent claims.

The invention will be explained in more detail below with reference to the drawings, in which:

FIG. 1 shows part of an article to be inspected which has a defect;

FIGS. 2*a*, *b* and *c* show the scanning response signals obtained at different focal depths;

Figure 1:
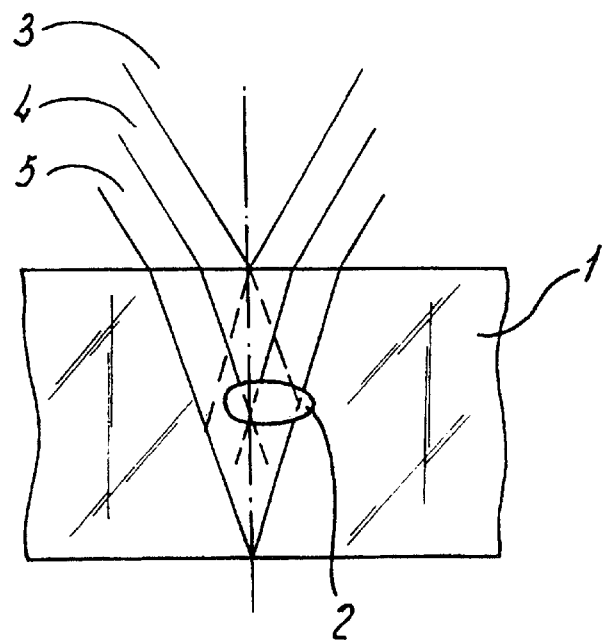

The aim of the invention is to detect defects in an article, for example an article in the form of a plate or disc. The defects can be particles, contaminants, damage and abnormalities in shape on a surface, as well as inclusions in a transparent or translucent medium. A glass plate 1 having an inclusion 2 is shown in FIG. 1 by way of example.

The article 1 is scanned by means of a scanning beam, which, for example, is produced by a laser and which is incident virtually perpendicularly on the front face of the article to be inspected. The light scattered by the article is collected and the collected light is converted into an electrical scanning response signal.

Figure 2:
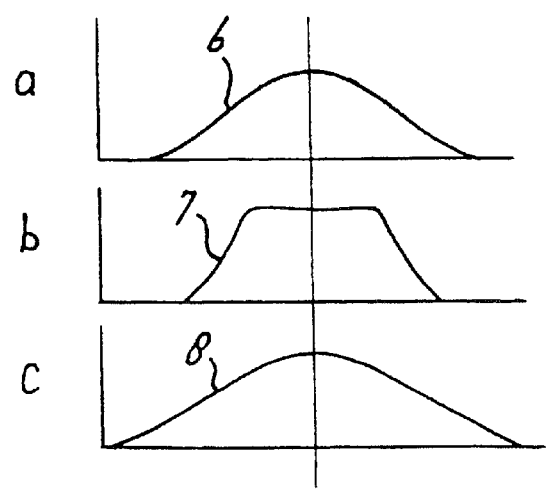

The scanning beam 3 is focused on the surface of the article 1 and, as a consequence of the inclusion 2, produces the electrical scanning response signal 6 shown in FIG. 2*a*, which scanning response signal is a pulse signal at the location of the defect 2.

The invention is based on the insight that in the presence of a defect the scanning response signal is dependent on the depth of the focal point in the article. The steepness of the flanks of the scanning response signals is greatest when the focal depth of the scanning light beam is equal to the depth of the defect or inclusion 2. Consequently, the depth of the inclusion can be accurately determined by determining the steepness of the flanks at two or more focal depths.

For the purposes of illustration, FIG. 1 shows three scanning light beams 3, 4 and 5 which are focused, respectively, on the front face of the article 1, at the depth of the inclusion and on the rear face of the article 1. The associated electrical scanning response signals 6, 7 and 8 are shown in FIGS. 2a, b and c respectively. The steepness of the scanning response signal will initially increase, as a function of a lateral shift in the focal point, to a maximum at the depth of the inclusion and will then decrease to the steepness of the scanning response signal 8.

In the example of a glass plate 1 shown in FIG. 1, light in the visible wavelength range can be used. When scanning, for example, a silicon wafer, however, a scanning light beam having a wavelength chosen such that the silicon wafer is transparent to the light beam must be used. In practice this means a wavelength of greater than 1,200 nm.

The depth of the defect can be determined in that at least two pulse scanning response signals are obtained in the presence of a defect. Said two scanning response signals are associated with two focal depths for the focal points of the scanning light beams. For example, a focal depth 0, that is to say focusing on the front face of the article to be inspected, and a deeper focal point are used. The number of scanning response signals can be obtained by scanning the article in its entirety a number of times, the scanning light beam having a different focal depth for each complete scan. As an alternative, a distinction between the scanning response signals can be obtained by using scanning light beams of different wavelengths and of different focal depths. The scanning response signals 6, 7 and 8 can, for example, be obtained in that the scanning beams 3, 4 and 5 have different wavelengths and, as is shown in FIG. 1, are focused on different depths in the article 1. With this method the scanning response signals from the scanning beams must be processed separately, for example by using filters prior to conversion.

The location or depth of a defect in the article can be determined the more accurately the greater the number of focal depths and the associated scanning response signals. For an advantageous and accurate determination it is possible, by interpolation between the focal depths used for two scanning response signals having a greater steepness than the remaining scanning response signals, to determine the focal depth of the scanning response signal that would have the greatest flank steepness, which latter depth then corresponds to the location of the defect.

Another embodiment makes use of a gradual increase in the focal depth of the scanning light beam in the direction thereof, the focal depth which is associated with the pulse scanning response signal having the steepest flanks being determined. This focal depth which has been determined is then an indication of the depth of the defect.

Figure 3:
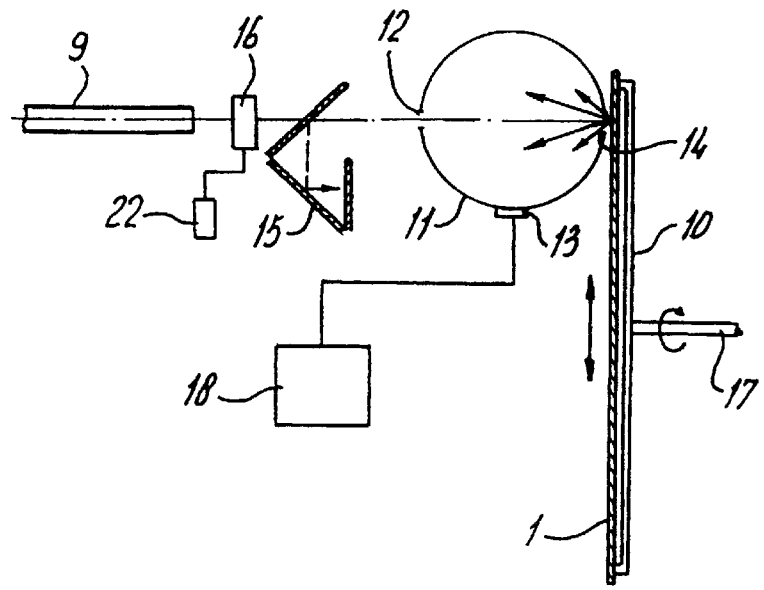
FIG. 3 shows an installation according to the invention for inspecting an article for defects.

FIG. 3 shows an installation for application of the invention. Said installation comprises a light source 9 in the form of a laser, the beam of which is perpendicular to the front face of the article 1 to be tested. The article 1 is held in an inspection plane by means of the article holder 10. Assuming that the article is a transparent plan-parallel plate 1, a collection device in the form of an integrating sphere 11 is located on one side of said plate. Said sphere has an opening with an opening edge 12 and an opposite opening with an edge 14, through which the laser beam is able to pass. Furthermore, each sphere also has an additional opening, through which a converter 13 in the form of a light-sensitive detector 13 is accessible to the scattered light originating from the plate to be inspected, which plate is in front of the opening with the edge 14.

In the case of a perfect article 1, the laser beam will pass through the integrating sphere 11 and said article without hindrance. Any light reflected by the article is collected in the light collection device 15. The installation also has a focusing device 16.

If there is a defect in the plate 1, part of the laser light will be scattered forwards. Said scattered light is captured in the integrating sphere 11 and as far as possible collected on the detector 13. When the plate 1 to be tested is rotated by rotation of the holder 10 about its axis 17, an electrical pulse scanning response signal is generated which can be obtained at the output of the detector 13. Said scanning response signal is fed to a processing unit. By rotating the plate to be tested about its axis and at the same time translating said axis in a direction perpendicular to the axis of rotation, the location and size of the defect can be determined. These data are determined by the processing unit 18 from the speed of rotation, the lateral shift per rotation and the signal from the detector 13.

Figure 4:
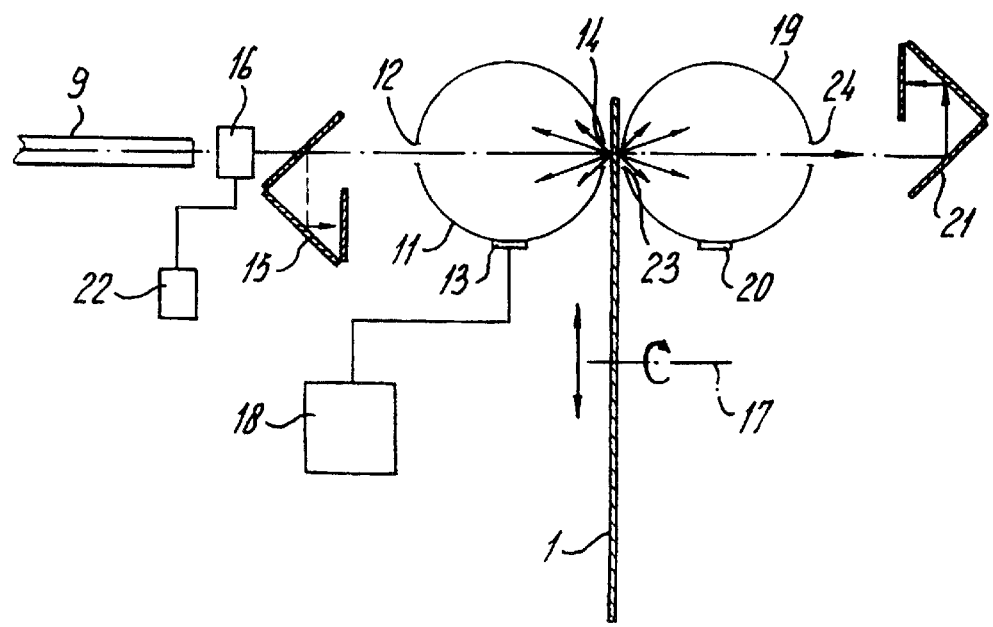
FIG. 4 illustrates another embodiment of the installation according to the invention.

If, however, the wavelength of the scanning light beam is chosen such that the article 1 is transparent to the light beam, it is then possible, as is shown in FIG. 4, to use a second integrating sphere 19 with detector 20. When a perfect article is inspected, the laser beam will pass through the first integrating sphere, the article 1 and the second integrating sphere and will be collected in the light collection device 21. The light specularly reflected at the surfaces of the article is collected, following any multiple reflection, in the light collection device 15 located between the laser 9 and the first integrating sphere 11.

Because two integrating spheres are used, the nature of the defect can be determined from the ratio of light scattered forwards and light scattered backwards, which ratios are determined experimentally for specific defects.

Multiple reflection is as far as possible counteracted by a scanning light beam which is incident perpendicularly on the faces of the article.

The installation described above functions most accurately when testing articles which do not cause diffuse scattering of light. In this case the method is a zero method; if there is no signal there is no defect, if there is a signal there is a defect. The installation could, however, also be used with articles which already scatter per se, provided that the scattering is reasonably constant over the article and the nature of the defect is such that the latter produces a greater variation in the detected signal than a possible variation in the scattering of the article without a defect. The applications of the abovementioned method and installation lie mainly in optics, the semiconductor industry and the industry involved in the production of storage media.

The installation is also provided with a focusing device, by means of which the focal point of a focused laser beam can be moved gradually or in discrete steps from the front face of the article 1 to the rear face. The shape of the scanning response signal is dependent on the focal depth and the depth of the defect in the article 1. The location of the defect can be deduced from the steepness of the flank of the scanning response signal when the object is scanned. In order to be able to determine the location of a defect, at least two measurements at two different axial positions of the focused beam must be carried out. A switching or control device 22, which switches or controls the focusing device 16, is provided for this purpose. By means of switching or control, a focal depth is chosen during a first total scan of the article, for example a focal depth 0, that is to say the scanning light beam is focused on the front face of the article 1. A greater focal depth, obtained by interaction between the focusing device 16 and the control device 22, is used for the subsequent complete scan. In this way a number of scanning response signals can be obtained, the flank steepnesses of which are measured by a flank steepness measuring device provided in the processing unit 18. A focal depth that belongs to the scanning response signal having the steepest front flank or rear flank can be determined from the data for the flank steepnesses and the focal depths by interpolation in an interpolation device in the processing unit. Said depth which is determined is thus a measure for the depth of the defect in the article. The various processing operations in the processing unit can be implemented by means of software.

The location of the defect in terms of height/depth is determined using an autofocus algorithm. For successive focus settings the recorded signal is measured as a function of the location. By differentiation of this recorded signal with respect to the location (2D and 2D, depending on the recording technique chosen), a maximum is found for a sharp image of the defect. A focus position from which the depth of the defect can be derived is associated with said maximum.

A similar type of measurement can also be carried out by working with a plurality of focused laser beams, the focal points of which are located spatially separated along an axis, which axis is perpendicular to the front face or rear face of the article. In this case the wavelengths of the laser beams used must firstly be so chosen that the article is transparent to said laser beams, whilst, moreover, the wavelengths must differ. Furthermore, the number of detectors per integrating sphere must correspond to the number of laser beams used, each detector being sensitive only to the wavelength of a specific laser beam (for example by means of a band filter).

The focusing device 16 can, for example, be set up such that, by means of the control device 22 interacting therewith, the focal depth of the scanning light beam in the direction hereof is gradually increased, whilst the article is continually scanned. The focal depth which is associated with the pulse scanning response signal having the steepest front or rear flank is then determined as an indication of the depth of the defect.

With the embodiments shown, the article 1 is scanned by a rotary movement thereof and a translation of the axis of rotation.

Figure 5:
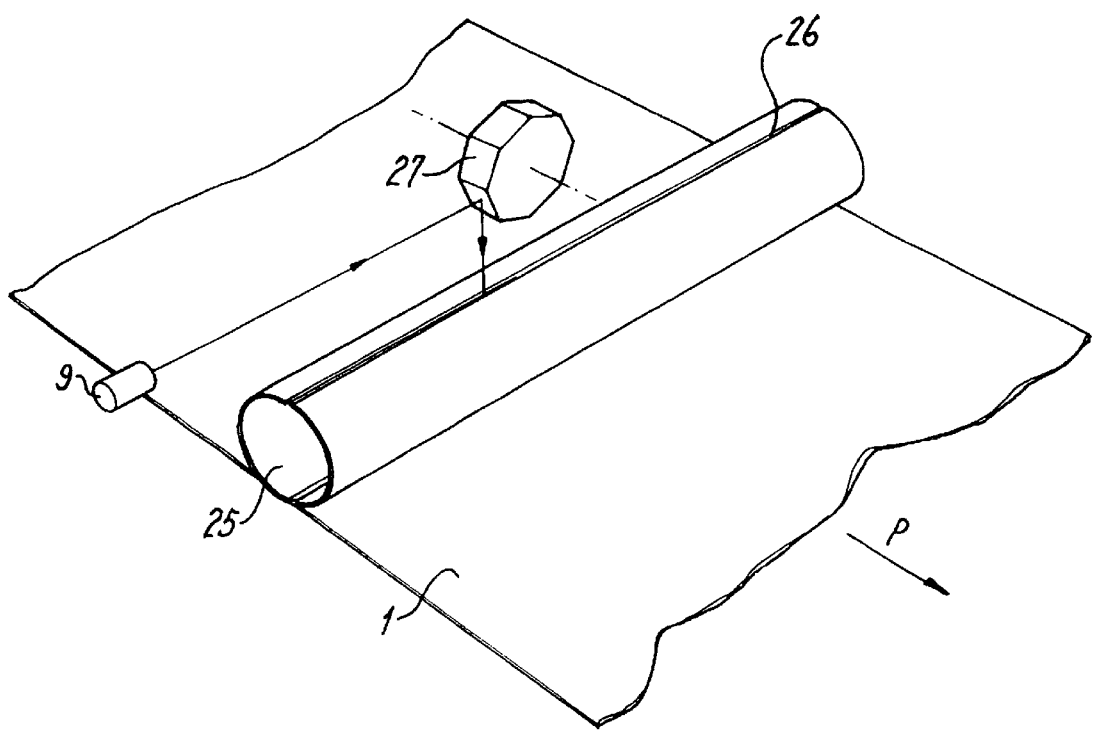
FIG. 5 shows yet a further embodiment of the installation according to the invention.

Embodiments which are suitable for articles having a shape which differs from a circular disc comprise, for example, an integrating collection device in the form of a cylinder (which is optionally segmented), which has been cut through in the longitudinal direction such that two slits located in an axial plane and running in the longitudinal direction of the cylinder have been produced. An embodiment of this type is shown in FIG. 5.

The article 1 to be inspected is transported past the integrating cylinder 25 in the direction of the arrow P. The integrating cylinder 25 is provided with slits, only slit 26 of which can be clearly seen. If the length of the cylinder 25 is equal to the width of the article, the cylinder is cut through such that the latter is divided into two halves. Illumination of the article can now take place by means of one or more light beams which scan the surface of the article through the slits in the cylinder, movable mirror surfaces being used to direct the beam(s). In FIG. 5 this is carried out by means of a polygon 27, which deflects the beam, originating from the light source 9, in the desired direction.

It is also possible to use a light line in conjunction with the integrating cylinder. A linear light beam is directed through the slits in the integrating cylinder onto the article to be inspected. In this case it is possible only to collect information along an axis. For complete determination of the location of the defect it is then possible to use an integrating sphere with light beam in the direction of the scanning light line to scan that line where a defect has been detected. An advantage of this latter embodiment could be a saving in time.

A microscope or another observation device can be used, in a manner which is not shown, on the installations described above, specifically in such a manner that, following a signal from the detectors, the defect that has given rise to the signal is brought within the field of view of the microscope.

This can be effected by stopping the defect within the field of view of the microscope or observation device or by aligning detector or measuring head and microscope such that, after it has passed by the measuring head, the defect is fed through the field of view of the microscope. Because the defect is now illuminated in the field of view of the microscope by a stroboscope or another pulse illumination device which is synchronised by the signal of the measuring head, the defect can be viewed without having to bring the object to be inspected to a standstill.

A CCD camera can also be mounted on the microscope, by which means the microscope image can be viewed via a monitor. After reading the images into a computer it is also possible to use image processing.

The addition of an article changer by means of which the throughput speed of the articles to be checked can be increased, also provides considerable advantages.

It is also possible to use a nozzle, by means of which the surface of the article to be inspected is cleaned with ionised air, and to switch this on when a surface defect is detected.

What is claimed is:

1. Method for inspecting an article (1) for defects (2), wherein the article (1) is scanned by means of a scanning light beam (3, 4, 5), the light scattered by the article (1) is collected and the collected light is converted into an electrical scanning response signal (6, 7, 8) which is fed to a processing unit (18) for processing the scanning response signals (6, 7, 8), a defect (2) in the article (1) giving rise to a pulse in the scanning response signal (6, 7, 8), characterised in that the light beam (3, 4, 5) has a wavelength such that the article (1) is transparent thereto, in that at least two scanning response signals (6, 7, 8) are obtained, each of which being associated with a focal point located in the direction of the light beam at a different depth in the article (1), and in that the location of the defect (2) in the direction of the light beam is determined from the steepness of the front and rear flanks of the pulses in the scanning response signals (6, 7, 8).

2. Method according to claim 1, characterised in that each of the at least two scanning response signals (6, 7, 8) is obtained by a different scanning operation of the article (1), and in that the scanning light beam (3, 4, 5) has a different focal point for each scanning operation.

3. Method according to claim 1, characterised in that each of the at least two scanning response signals (6, 7, 8) is obtained by a scanning light beam (3, 4, 5) of a different wavelength and having a different focal point.

4. Method according to claim 1, characterised in that the focal points of the scanning light beams (3, 4, 5) are distributed over the depth of the article (1) to be inspected, that two scanning response signals (6, 7, 8) having a pulse with steeper flanks than the remaining scanning response signals are determined and that the depths in the article of the focal points of the scanning light beams (3, 4, 5) producing said determined two scanning response signals (6, 7, 8) are determined, in which the depth of the defect is an interpolation of the depths of the said focal points.

5. Method according to claim 1, characterised in that during repeated scanning of the article, the focal points of the scanning light beams (3, 4, 5) are gradually shifted over the depth of the article (1) to be inspected that the scanning response signal (6, 7, 8) having a pulse with the steepest flanks with respect to the remaining scanning response signals is determined and that the depth in the article of the focal point of scanning light beam (3, 4, 5) producing said determined scanning response signal (6, 7, 8) is determined, in which the determined depth is an indication for the depth of the defect.

6. Installation for inspecting an article (1) for defects (2), comprising an article holder (10) for holding an article (1) to be inspected in an inspection plane, a light source (9), which emits a scanning light beam (3, 4, 5) for scanning the article (1) to be inspected, a collection device (11, 19, 25) for collecting the light scattered by the article (1), a converter (13), for converting the collected light into an electrical scanning response signal (6, 7, 8) and a defect (2) in the article (1) giving rise to a pulse in the scanning response signal, and a processing unit (18) connected to the output of the converter (13) for processing the scanning response signal (6, 7, 8), characterised in that the scanning light beam (3, 4, 5) has a wavelength such that the article (1) is transparent to said beam, that means are present for obtaining at least two scanning response signals (6, 7, 8), each of which being associated with a focal point located in the direction of the scanning light beam at a different depth in the article (1), and in that the processing unit (18) is provided with a flank steepness measuring device for measuring the steepness of the front and rear flanks of the pulses in the scanning response signals (6, 7, 8) fed thereto, and an evaluation device for determining the location of a defect from the measured flank steepnesses.

7. Installation according to claim 6, characterised in that a switching or control device (22) is provided which after each complete scanning operation on the article (1) to be inspected switches or changes the focal depth of the scanning light beam to another value for the next scanning operation on the article.

8. Installation according to claim 6, characterised in that at least two light sources are present, the scanning light beams of which have different wavelengths and different focal depths and in that there is one converter for each wavelength.

9. Method according to claim 6, characterised in that the focal points of the scanning light beams (3, 4, 5) are distributed over the depth of the article (1) to be inspected, and that the processing unit (18) is provided with means for determining two scanning response signals (6, 7, 8) having a pulse with steeper flanks than the remaining scanning response signals and means for determining the depths in the article of the focal points of the scanning light beams (3, 4, 5) producing said determined two scanning response signals (6, 7, 8), in which the depth of the defect is an interpolation of the depths of the said focal points.

10. Method according to claim 6, characterised in that during repeated scanning of the article, the focal points of the scanning light beams (3, 4, 5) are gradually shifted over the depth of the article (1) to be inspected, and that the processing unit (18) is provided with means for determining the scanning response signal (6, 7, 8) having a pulse with the steepest flanks with respect to the remaining scanning response signals and means for determining the depth in the article of the focal point of scanning light beam (3, 4, 5) producing said determined response signal (6, 7, 8) in which the determined depth is an indication for the depth of the defect.

11. Installation according to claim 6, characterised in that a collection device (11, 19) with associated converter (13, 20) for the scattered light is provided at either side of the inspection plane of the article holder (10).

12. Installation according to claim 11, characterised in that a light collector (15, 21) is added to one or both collection devices to capture specularly reflected light.

13. Installation according claim 6, characterised in that the holder for the article to be inspected is rotatable about a central axis of rotation perpendicular to the inspection plane for the article to be inspected, wherein the axis of rotation is translatable in a direction perpendicular thereto and wherein the collection device (11) or devices (11, 19) is constructed as an integrating sphere.

14. Installation according to claim 6, wherein the collection device (11) or devices (11, 19) is formed by an integrating cylinder (25) having two diametrically opposed slits (26), running in the longitudinal direction of the cylinder, to allow passage of the scanning light.

15. Installation according to claim 14, wherein the article to be inspected and the integrating cylinder are offset with respect to one another in a direction perpendicular to the plane through the slits (26) in the integrating cylinder (25) and one or more light beams scan the surface of the article through the slits by means of movable mirror surfaces (27).

16. Installation according to claim 14, wherein the light source is formed by a line light source and a linear scanning light beam is produced which propagates through the slits in the integrating cylinder (25) and produces a scanning light line on the article and wherein an integrating sphere with light beam is provided adjacent to the integrating cylinder (25) for scanning the article in the direction of the line on which a defect has been detected.

17. Installation according to claim 6, characterised in that a stroboscope is provided which is synchronised by the defect detection.

* * * * *